United States Patent
Rensen et al.

(10) Patent No.: US 7,453,564 B2
(45) Date of Patent: Nov. 18, 2008

(54) METHOD OF DETERMINING A PROPERTY OF A FLUID AND SPECTROSCOPIC SYSTEM

(75) Inventors: Wouter Harry Rensen, Eindhoven (NL); Michael Cornelis Van Beek, Eindhoven (NL); Marjolein Van Der Voort, Valkenswaard (NL); Bernardus Leonardus Bakker, Nijmegen (NL); Gerhardus Wilhelmus Lucassen, Eindhoven (NL); Teunis Willem Tukker, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 115 days.

(21) Appl. No.: 10/595,358

(22) PCT Filed: Oct. 15, 2004

(86) PCT No.: PCT/IB2004/052110

§ 371 (c)(1),
(2), (4) Date: Apr. 12, 2006

(87) PCT Pub. No.: WO2005/037094

PCT Pub. Date: Apr. 28, 2005

(65) Prior Publication Data

US 2007/0070328 A1 Mar. 29, 2007

(30) Foreign Application Priority Data

Oct. 17, 2003 (EP) .................................. 03103844

(51) Int. Cl.
*G01J 3/00* (2006.01)

(52) U.S. Cl. ........................ 356/300; 356/301; 356/317

(58) Field of Classification Search ................. 356/301, 356/317, 326; 600/322
See application file for complete search history.

(56) References Cited

U.S. PATENT DOCUMENTS

| 4,853,917 | A  | * | 8/1989 | Koyama et al. | 369/44.41 |
|---|---|---|---|---|---|
| 6,193,372 | B1 | * | 2/2001 | Okumura et al. | 351/221 |
| 6,208,749 | B1 |   | 3/2001 | Gutkowicz-Krusin et al. | |
| 6,542,246 | B1 |   | 4/2003 | Toida | |
| 6,609,015 | B2 | * | 8/2003 | Lucassen et al. | 600/322 |
| 6,687,520 | B2 |   | 2/2004 | Lucassen et al. | |
| 6,889,075 | B2 | * | 5/2005 | Marchitto et al. | 600/473 |
| 6,913,603 | B2 | * | 7/2005 | Knopp et al. | 606/10 |
| 6,997,923 | B2 | * | 2/2006 | Anderson et al. | 606/9 |
| 7,217,266 | B2 | * | 5/2007 | Anderson et al. | 606/12 |
| 2002/0016533 | A1 |   | 2/2002 | Marchitto et al. | |
| 2002/0091322 | A1 |   | 7/2002 | Chaiken et al. | |
| 2002/0161357 | A1 | * | 10/2002 | Anderson et al. | 606/9 |

(Continued)

FOREIGN PATENT DOCUMENTS

EP     1658487 A1     5/2006

(Continued)

*Primary Examiner*—Kara E Geisel

(57) ABSTRACT

A property of a fluid is determined spectroscopically, such as for the purposes of in vivo blood analysis. First the position of a volume of interest through which the fluid flows is determined by an optical detection step by making use of an objective. Preferably the optical detection step is an imaging step. Next the objective is moved to bring the focal point of the objective into coincidence with the volume of interest. In this position an optical spectroscopic step is performed. This has the advantage that the measurement beam for performing the optical spectroscopy travels along the optical axis for optimum efficiency.

18 Claims, 8 Drawing Sheets

U.S. PATENT DOCUMENTS

Figure 1:
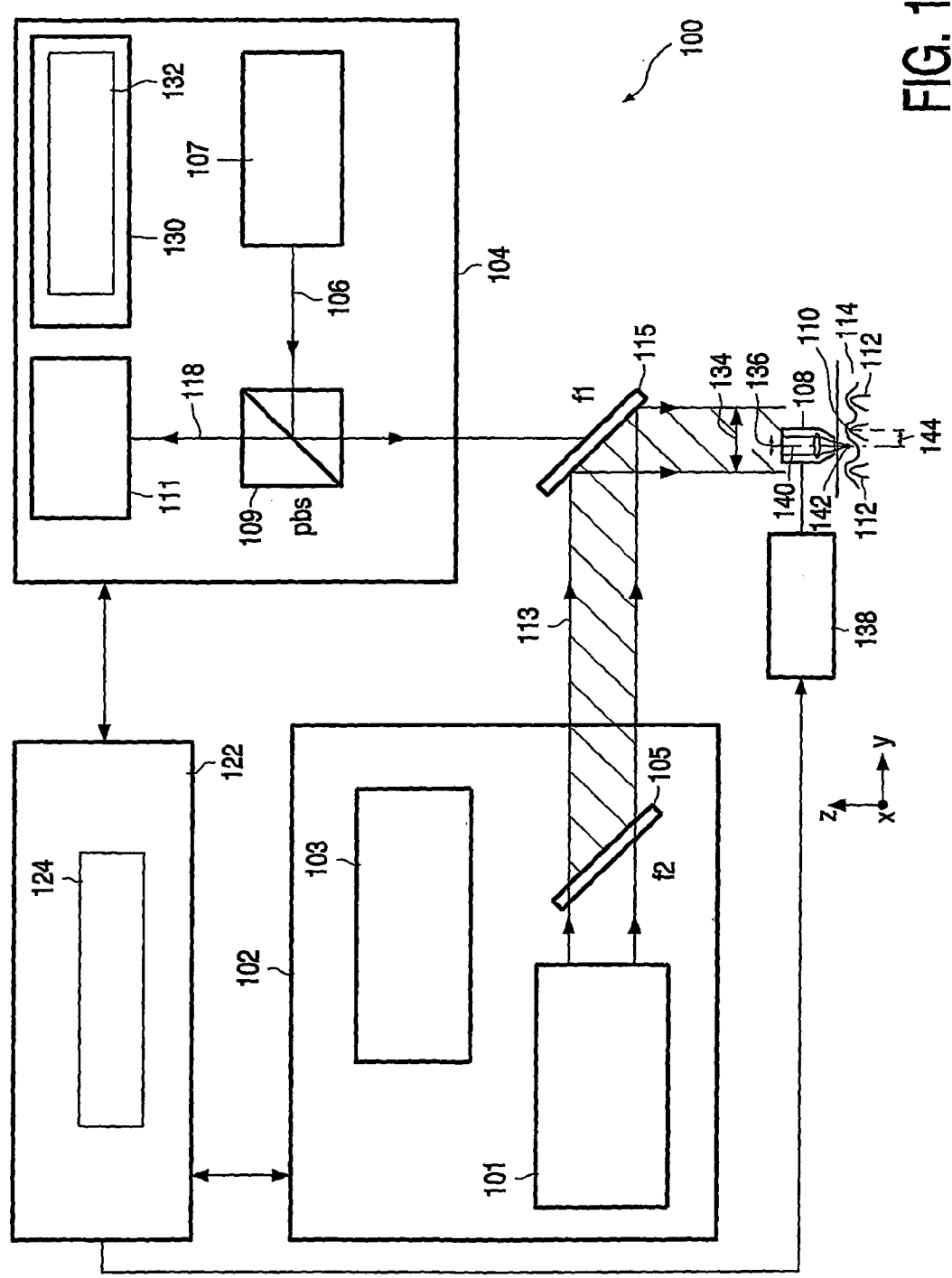

| | | |
|---|---|---|
| 2004/0096913 A1 | 5/2004 | Boddeke et al. |
| 2006/0235308 A1 | 10/2006 | Van Beek et al. |
| 2007/0049830 A1 | 3/2007 | Hendriks et al. |

FOREIGN PATENT DOCUMENTS

| | | | |
|---|---|---|---|
| EP | 1605819 B1 | | 5/2007 |
| WO | WO9009756 | A1 | 9/1990 |
| WO | WO9222793 | A1 | 12/1992 |
| WO | WO9963328 | A1 | 12/1999 |
| WO | WO02057758 | A1 | 7/2002 |
| WO | WO02057759 | A1 | 7/2002 |
| WO | WO2004082474 | A1 | 9/2004 |
| WO | WO2005015179 | A1 | 2/2005 |

* cited by examiner

METHOD OF DETERMINING A PROPERTY OF A FLUID AND SPECTROSCOPIC SYSTEM

The present invention relates to the field of optical spectroscopy, and more particularly to the usage of optical spectroscopic techniques for analytical purposes.

Usage of optical spectroscopic techniques for analytical purposes is as such known from the prior art. U.S. Pat. No. 6,687,520 and US 2004/0096913 show spectroscopic analysis apparatuses for in vivo non-invasive spectroscopic analysis of the composition of blood flowing through a capillary vessel of a patient. The capillary vessel is imaged by a monitoring system and an excitation beam is directed to the capillary vessel in order to perform the spectroscopic analysis. For example near-infrared radiation is used for excitation of Raman scattering. The Raman scattered radiation is spectroscopically analyzed for determination of blood properties.

The in vivo analysis of blood has a number of advantages as compared to prior art blood analysis, where blood is drawn from the arm, for example with the use of a needle, and the blood sample is analyzed in a chemical laboratory. The transport and the analysis take a considerable amount of time, varying between two days and typically 20 minutes in emergency situations. In contrast, in vivo blood analysis enables to instantaneously and continuously monitor the properties of blood without pain and risk of infections for the patient.

The present invention therefore aims to provide an improved method of non-invasive determination of a property of a fluid which flows through a biological tubular structure, in particular for in vivo non-invasive analysis of blood flowing through the capillary vessels in the skin of a patient.

The present invention provides a method of determining a property of a fluid. First the position of a volume of interest through which the fluid flows needs to be determined by means of an optical detection step. This is done by means of an optical objective. Preferably an imaging method is employed for determination of the position of the volume of interest, such as a pattern recognition technique for determining the positions of blood vessels through which the blood flows.

Suitable imaging methods include orthogonal polarized spectral imaging (OPSI), confocal video microscopy (CVM), optical coherence tomography (OCT), confocal laser scanning microscopy (CLSM) and Doppler based imaging. Corresponding imaging techniques are disclosed in US 2004/0096913 US 2007/0049830 and US 2006/0235308, respectively, the whole of which is herein incorporated by reference.

The position of the volume of interest which is determined by means of the optical detection is not necessarily located on the optical axis of the objective. In this situation the objective is moved such that the focal point of the objective is positioned in the volume of interest.

Next an optical spectroscopic step is performed for determining the property of the fluid in the volume of interest. For this purpose a measurement beam is directed along the optical axis of the objective and focused within the volume of interest. This has the advantage that the optical spectroscopic step can be performed with optimum efficiency and accuracy. This is due to the fact that the objective performs best when the laser beam passes along its optical axis, i.e. optical aberrations will be minimal. Further, the efficiency of the collection of the return radiation is also optimal.

In this way the invention enables to use a relatively inexpensive objective for performing a highly efficient and accurate optical spectroscopy for determining a property of the fluid. As far as applications for in vivo analysis of blood are concerned the present invention is particularly advantageous as it enables to focus the measurement beam within the selected blood vessel without a need to translate the skin after the optical detection step. This in turn enables a compact design of a measurement head which is completely sealed for optimal hygiene. As no translation of the skin is required measurements can be performed quickly and with optimal comfort for the patient.

In accordance with a preferred embodiment of the invention the coverage of the measurement beam is greater than the objective opening, i.e. the objective is "overfilled". This enables to move the objective in order to position the focal point of the objective in the volume of interest while the objective opening remains within the coverage of the measurement beam. This has the advantage that only the objective is moved while the measurement beam remains stationary.

In accordance with a further preferred embodiment of the invention a reflective optical element which is coupled to the objective is used to enable larger translations of the objective. In this case the measurement beam has a direction which is perpendicular to the optical axis of the objective when it impinges upon the reflective optical element which directs the measurement beam onto the objective opening along the optical axis of the objective.

This can be combined with overfilling of the objective opening. In this instance the reflective optical element is only moved together with the objective when the tolerance provided by the overfilling is not sufficient to position the focal point within the volume of interest. This embodiment is particularly advantageous as the degree of overfilling can be minimal and efficient usage is thus made of the available laser power.

In accordance with a further preferred embodiment of the invention a further reflective optical element is used which is rotated to direct the measurement beam onto the reflective optical element which is coupled to the objective. In this way large translations of the objective in two dimensions are enabled while keeping the measurement beam stationery.

In accordance with a further preferred embodiment of the invention the light path and optical pick up unit of an optical disk drive are used as an inexpensive and compact mechanism to translate the objective. The same pick up unit can also be used to focus the objective on the capillaries.

If blood capillaries are not distributed densely enough, it is advantageous to combine the pick up unit with a one-dimensional translation stage of any sort. With the aid of reflective optics a large rectangular area can thus be covered.

In accordance with a preferred embodiment of the invention the optical detection step is performed repetitively in order to track the position of the volume of interest. The objective is moved such that the focal point follows the movement of the volume of interest. This is particularly advantageous for monitoring the property of the fluid over longer time intervals, such as for monitoring the blood composition during surgery.

In accordance with a further preferred embodiment of the invention confocal Raman spectroscopy is used. Light from a Raman excitation laser is directed towards the detection volume through the objective and Raman scattered radiation is collected by the same objective for spectroscopic analysis. It is to be noted that the present invention is not restricted to spontaneous Raman spectroscopy but that other optical spectroscopic techniques can also be used.

This includes (i) other methods based on Raman scattering including stimulated Raman spectroscopy and coherent anti-stokes Raman spectroscopy (CARS), (ii) infra-red spectroscopy, in particular infra-red absorption spectroscopy, Fourier transform infra-red (FTIR) spectroscopy and near infra-red (NIR) diffuse reflection spectroscopy, (iii) other scattering spectroscopy techniques, in particular fluorescence spectroscopy, multi-photon fluorescence spectroscopy and reflectance spectroscopy, and (iv) other spectroscopic techniques such as photo-acoustic spectroscopy, polarimetry and pump-probe spectroscopy. Preferred spectroscopic techniques for application to the present invention are Raman spectroscopy and fluorescence spectroscopy.

Figure 2:
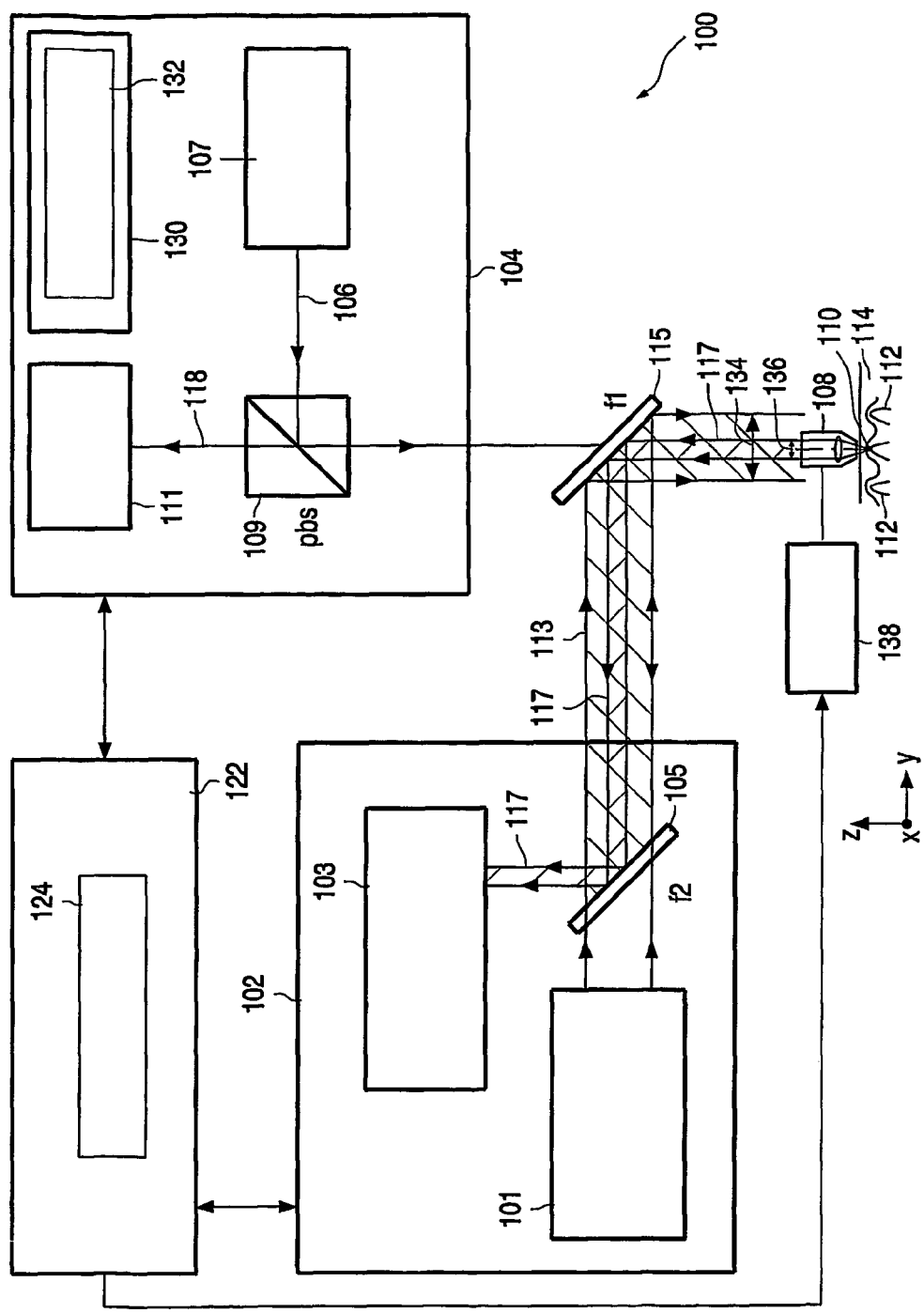
Figure 3:
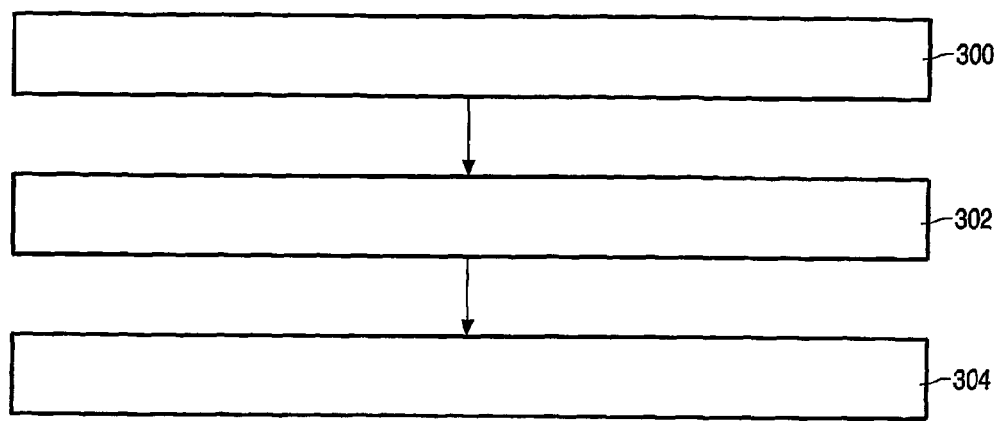
Figure 4:
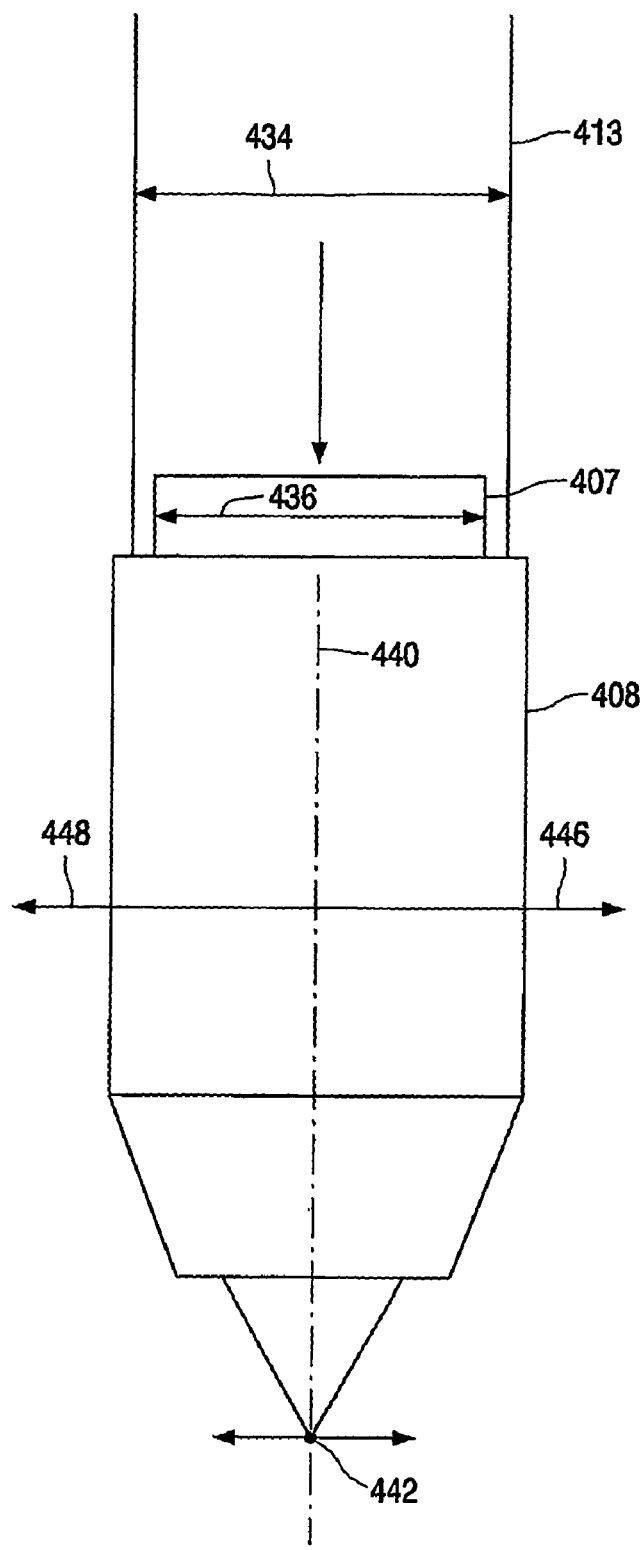
Figure 5:
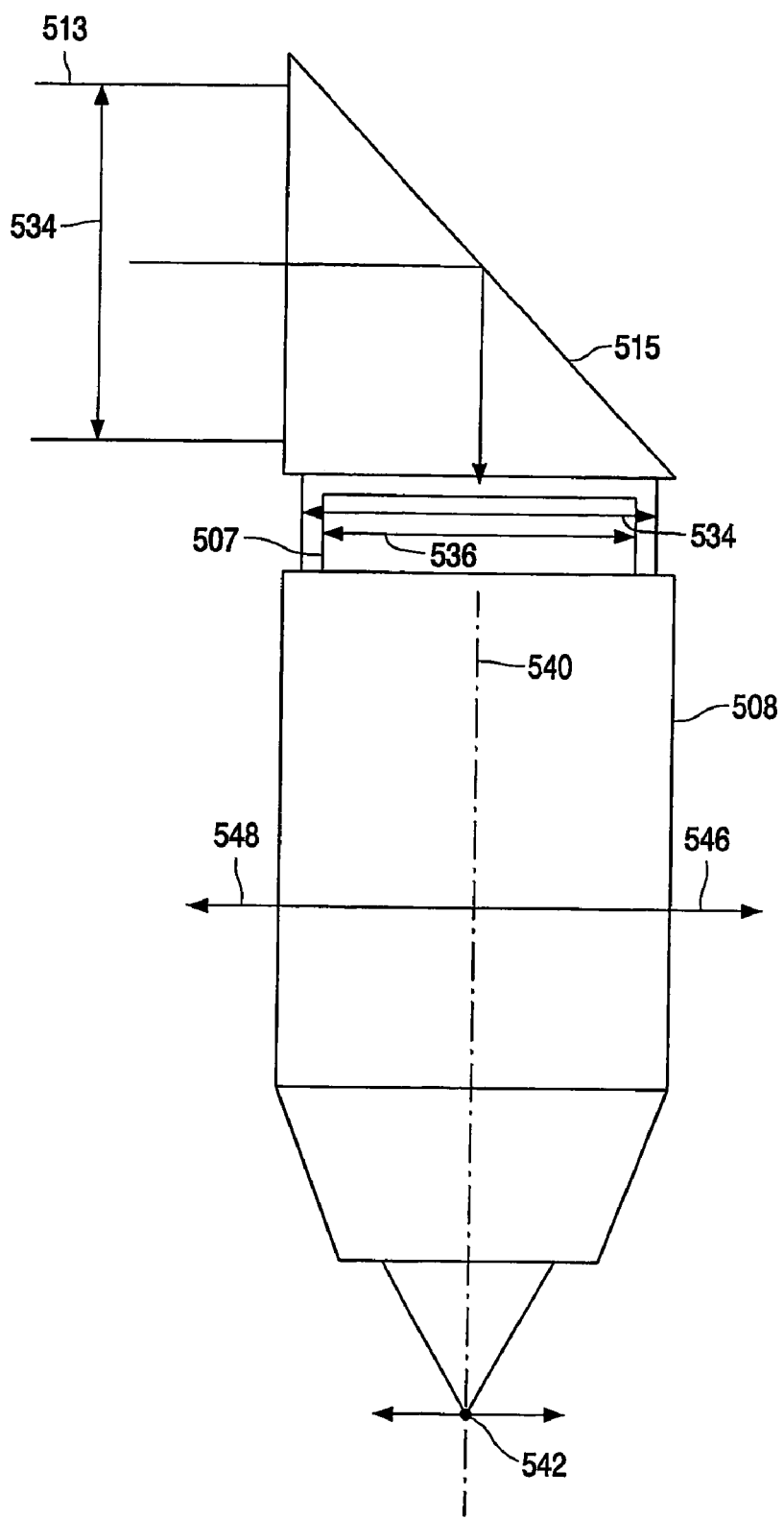
Figure 6:
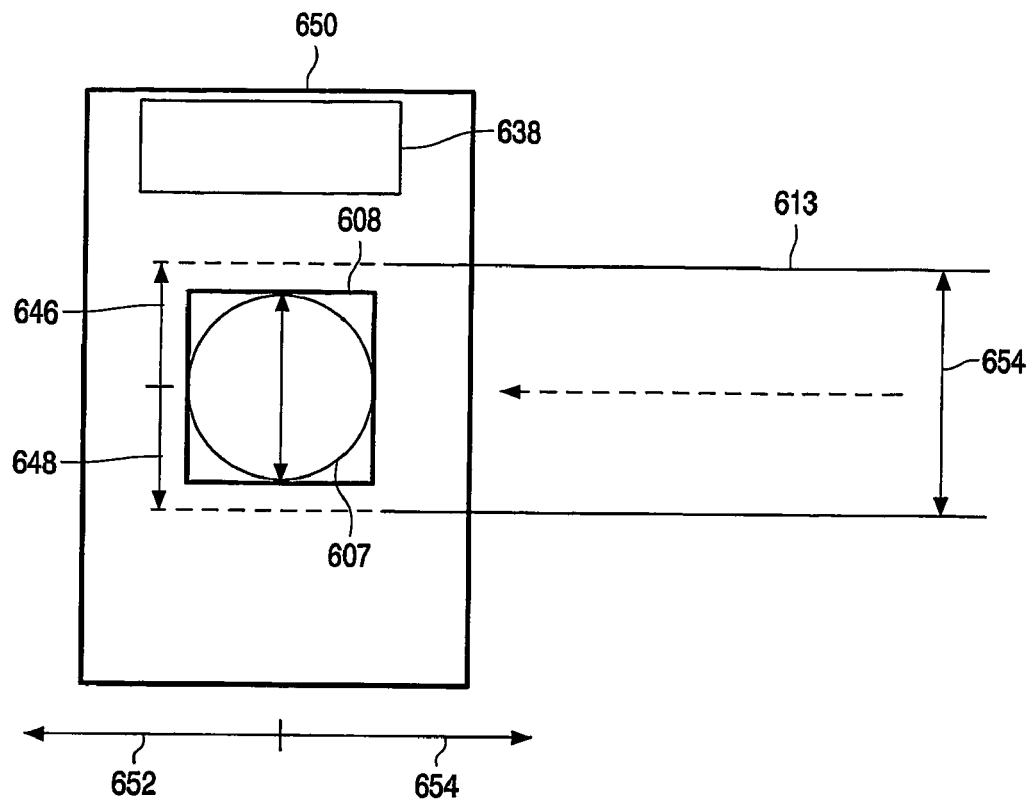
Figure 7:
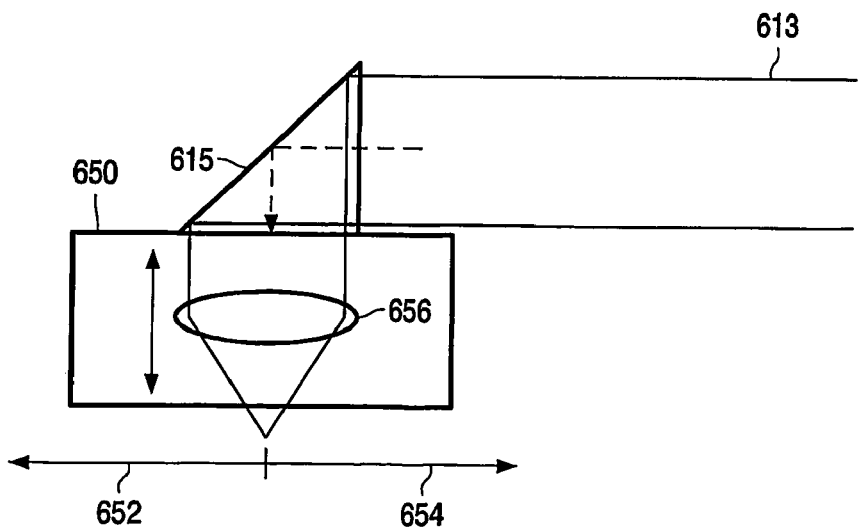
Figure 8:
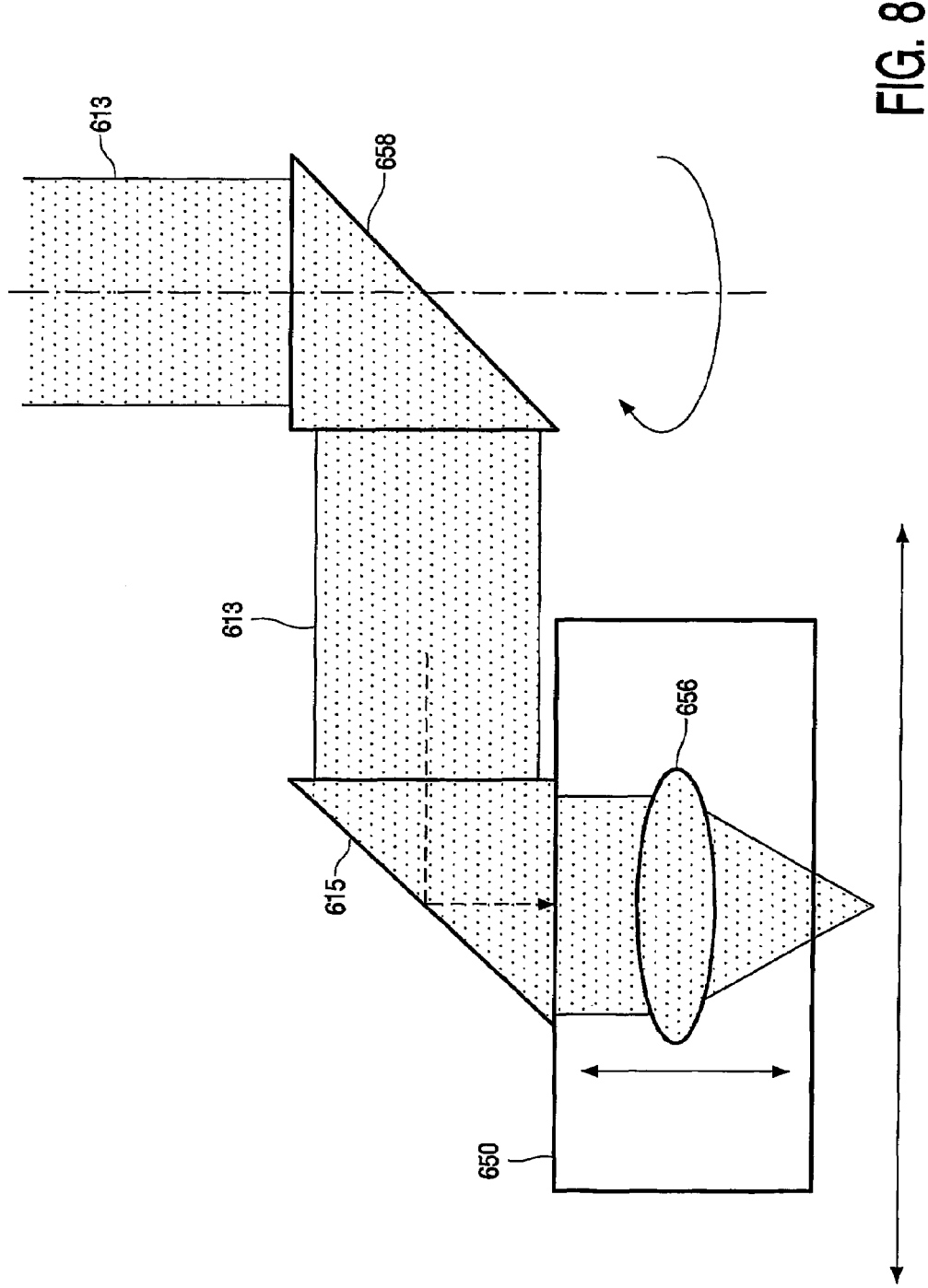
Figure 9:
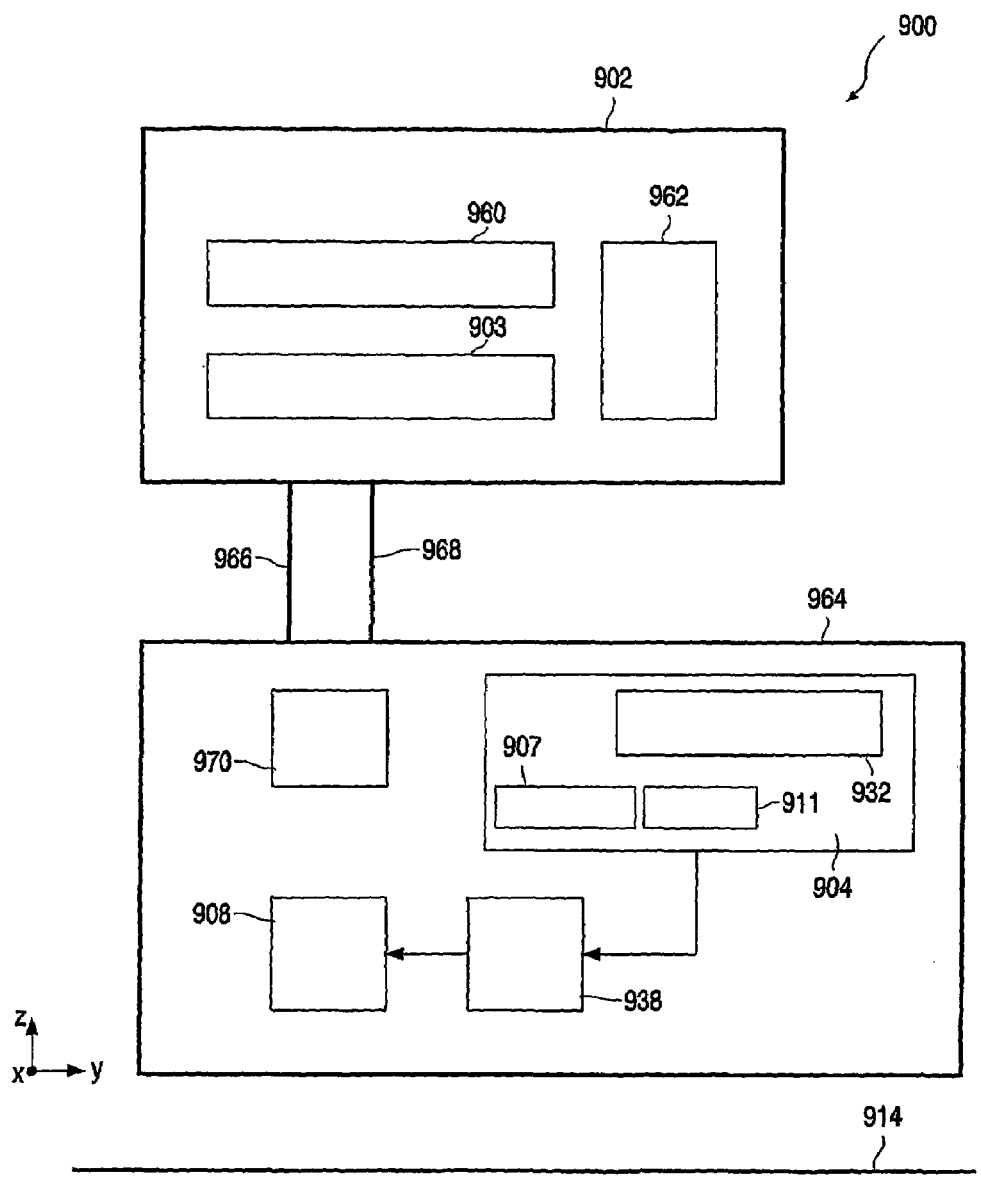

The following preferred embodiments of the invention will be described in greater detail by making reference to the drawings in which:

FIG. 1 is a block diagram of an embodiment of a spectroscopic system of the invention, FIG. 2 illustrates operation of the spectroscopic system of FIG. 1, FIG. 3 is a flow chart being illustrative of a preferred embodiment of a method of the invention, FIG. 4 is illustrative of over filling the objective for the purpose of moving the objective laterally within the coverage of the measurement beam, FIG. 5 shows a reflective optical element which is coupled to the objective in order to enable larger translations of the objective in one direction, FIG. 6 shows a top view of an optical pick up unit, FIG. 7 shows a side view of the optical pick up unit of FIG. 5, FIG. 8 shows a pick up unit with a reflective optical element which is rotatably mounted, FIG. 9 is a block diagram of a measurement head coupled to a base station.

FIG. 1 shows apparatus 100 which can be used for determining a property of a fluid which flows through a biological tubular structure, such as blood flowing through a capillary vessel under the skin of a patient. Apparatus 100 has Raman spectroscopic system 102 for confocal Raman spectroscopy and imaging system 104.

Raman spectroscopic system 102 has laser light source 101 and spectrometer 103. Raman return radiation is directed to spectrometer 103 by dichroic mirror 105 of spectroscopic system 102.

Imaging system 104 has light source 107 that provides an incident imaging light beam 106. Imaging light beam 106 is directed to objective 108 over polarizing beam splitter 109 and dichroic mirror 115.

Imaging light beam 106 of light source 107 causes return light 118 which is received by imaging system 104, e.g. CCD camera 111. Other types of cameras which can be used are CMOS and photodiode array cameras or others. Furthermore, imaging system 104 has processor 130 for running computer program 132 for the purpose of position detection.

Laser light source 101 of Raman spectroscopic system 102 provides incident laser light beam 113 which is reflected on dichroic mirror 115 and directed towards objective opening of objective 108. Width 134 of incident laser light beam 113 is larger than width 136 of the objective opening of objective 108.

Objective 108 is mechanically coupled to actuator 138. For example, actuator 138 is a motorized mechanical translation stage for moving objective 108 within the xy-plane. By means of the actuator 138 the focal point needs to be positioned in the volume of interest in three dimensions: x, y and z. Positioning the focal point in the volume of interest in the z-direction is normally referred to as focusing. In addition, actuator 138 is also used to move the objective in the z-direction for focusing in addition to the movement in the x, y-plane. Alternatively, actuator 138 is a piezo-electric element or another electromechanical translation stage.

Raman spectroscopic system 102, imaging system 104 and actuator 138 are coupled to controller 122. Controller 122 has control program 124 for controlling all operations of apparatus 100.

For performing an in vivo blood analysis by means of apparatus 100 a patient places a body portion with skin 114 under objective 108. Skin 114 has a number of blood vessels 112.

When apparatus 100 is activated, control program 124 issues a control signal to imaging system 104. In response light source 107 provides imaging light beam 106 for taking a picture of skin 114 by means of CCD camera 111 through objective 108. The picture is analyzed by program 132 in order to detect at least one of the blood vessels 112. In this way detection volume 110 for performing the spectroscopic blood analysis is determined. In the example considered here detection volume 110 is not on optical axis 140 of objective 108.

The position of detection volume 110 is communicated from the program 132 to control program 124. Control program 124 determines the distance of detection volume 110 from optical axis 140 of objective 108. For determining the actual position of objective 108 a position sensor can be provided which is also coupled to controller 122 (not shown in the drawing). However, it is preferred to use the imaging system 104 for verification of the change of position of objective 108; this way a feedback circuit is provided.

After having determined the distance between the position of detection volume 110 and optical axis 140, control program 124 issues a control signal to actuator 138 in order to displace objective 108 in the xy-plane in order to position optical axis 140 on detection volume 110. This way the focal point 142 of objective 108 is moved inside detection volume 110; this is illustrated in FIG. 2 after the objective 108 has been moved by distance 144 between optical axis 140 and detection volume 110.

It is to be noted that movement of objective 108 in the xy-plane is limited by width 134 of incident laser light beam 113. This enables to keep laser light source 101 as well as dichroic mirrors 105 and 115 stationery.

After the objective 108 has been moved by distance 144 in order to bring optical axis 140 to detection volume 110, control program 124 issues a control signal to Raman spectroscopic system 102. In response, Raman spectroscopic system 102 provides incident laser light beam 113 from laser light source 101 which is directed along optical axis 140 of objective 108 to detection volume 110.

The portion of incident laser light beam 113 that does not impinge upon the objective opening of objective 108 is not used for the spectroscopy. Such a situation is also referred to as "over filling" of objective 108. It is important to note that the portion of incident laser light beam 113 which impinges upon objective opening of objective 108 is directed along optical axis 140 to focal point 142 within detection volume 110.

This results in Raman return light beam 117 which has width 136 of the objective opening of objective 108. The Raman return light beam 117 is received by spectrometer 103 via dichroic mirrors 115 and 105. Spectrometer 103 performs a spectroscopic analysis of Raman return light beam 117. This way one or more properties of the blood flowing through detection volume 110 are determined.

FIG. 3 shows a corresponding flow chart. In step 300 an imaging method is performed in order to determine the position of a volume of interest, e.g. a detection volume for performing blood analysis. The imaging is performed by means of an optical objective.

In step 302 the objective is moved such that the focal point of the objective is brought into the volume of interest. In step 304 Raman spectroscopy or another optical spectroscopic method is performed by directing a measurement beam through the objective to the volume of interest and collecting the return radiation caused by the measurement beam from the volume of interest by means of the objective.

FIG. 4 is an enlarged view of an objective which is used both for optical detection of a volume of interest and optical spectroscopy in accordance with the principles of the invention. Elements of FIG. 4 which correspond to elements of FIGS. 1 and 2 are designated by like reference numerals having added 300.

Objective 408 has objective opening 407. Objective opening 407 has width 436. Objective 408 has optical axis 440 and focal point 442.

Objective 408 is first used to determine the position of a volume of interest by means of an optical detection step. The position of the volume of interest may not be located on optical axis 440 as explained above by way of example and illustrated in FIG. 1.

For performing the subsequent optical spectroscopic step objective 408 is moved in direction 446 or opposite direction 448 in order to move the focal point 442 to the volume of interest. In the preferred embodiment considered here this movement is limited by the extent of measurement beam 413, i.e. its width 434. Objective 408 is over filled by measurement beam 413. In other words measurement beam 413 has width 434 which is larger than width 436 of objective opening 407.

The direction of measurement beam 413 is parallel to optical access 440. As a consequence, the portion of measurement beam 413 which impinges upon objective opening 407 is also parallel to optical axis 440 and is thus directed to focal point 442. From there return radiation is collected by objective 408 and transmitted to a spectrometer for spectroscopic analysis.

FIG. 5 shows an alternative embodiment where like elements are designated by like reference numerals as in FIG. 4 having added 100. In the embodiment of FIG. 5 incident laser light beam 513 has a direction which is perpendicular to optical axis 540 of objective 508. Incident laser light beam 513 is reflected by optical element 515 into the direction of optical axis 540. As in the embodiments of FIGS. 1, 2 and 4 width 534 of incident laser light beam 513 is larger than width 536 of objective opening 507 of objective 508.

Objective 508 can be moved into directions 546 and 548 while incident laser light beam 513 and optical element 515 remains stationery as long as objective opening 507 of objective 508 remains completely within coverage of incident laser light beam 513. When objective 508 needs to be moved by a larger distance to bring focal point 542 to volume of interest optical element 515 is moved together with objective 508 while the position of incident laser light beam 513 remains unchanged. In this way large translations of objective 508 into directions 546 and 548 are enabled. For example optical element 515 is a prism or a mirror (cf. dichroic mirror 115 in the embodiment of FIGS. 1 and 2).

FIG. 6 shows a top view of pickup unit 650. Pick up unit 650 carries objective 608. Pick up unit 650 has actuator 638 for controllably moving objective 608 into directions 646 and 648 as well as in directions 652 and 654. The position of incident laser light beam 613 is fixed.

As in the embodiments considered above width 654 of laser light beam 613 is larger than width 636 of objective opening 607. Thus the movement of objective 608 into directions 646 and 648 is limited by the coverage of objective opening 607 by incident laser light beam 613. The limitation of the movement of objective 608 into directions 646 and 648 is indicated by the dashed lines in FIG. 6.

FIG. 7 shows a side view of pick up unit 650. Pick up unit 650 carries reflective optical element 615 which directs incident laser light beam 613 onto lens 656 of objective 608. This enables movement of objective 608 together with reflective optical element 615 by larger distances into directions 652 and 654 while the position of incident light beam 613 remains unchanged. In addition, lens 656 can be moved vertically for the purpose of focusing.

One way of implementing pick up unit 650 is by means of an optical pick up unit which is used in optical disk drives, such as CD players.

In case a larger displacement of objective 608 into directions 646 or 648 is required, an additional reflective optical element 658 can be utilized as illustrated in FIG. 8. Reflective optical element 658 is rotatably mounted on a swiveling arm (not shown in FIG. 8). Alternatively, all optical components depicted in FIG. 7 are mounted on the swiveling arm in order to best maintain the optical alignment. By rotation of reflective optical element 658, the direction of the reflected laser light beam 613 is varied in directions 646 or 648 (cf. FIG. 6) such that objective 608 can be moved correspondingly into these directions.

FIG. 9 shows a block diagram of an alternative embodiment of spectroscopic apparatus 900. Spectroscopic apparatus 900 has base station 902 which comprises spectrometer 903, display unit 960 and program 962.

Base station 902 is coupled to measurement head 964 by means of optical fibres 966 and 968.

Measurement head 964 has imaging system 904 comprising light source 907, camera 911 and program 932. Imaging system 904 is coupled to actuator 938 which is mechanically coupled to objective 908 for moving the objective 908 in the xy-plane. Further, measurement head 964 has optical elements 970 for directing an incident measurement beam received over optical fibre 966 to objective 908 and for coupling return radiation which is collected by objective 908 into optical fibre 968 for transmission to spectrometer 903.

In operation a patient places measurement head 964 on his or her skin. Light source 907 of imaging system 904 provides an imaging light beam (cf. imaging light beam 106 of FIG. 1) which is directed by optical element 970 through objective 908 to skin 914.

By means of camera 911 a picture is taken of the skin 914, which is analyzed by means of program 932 for detection of blood vessels and selection of a detection volume within one of the blood vessels. Imaging system 904 controls actuator 938 to move objective 908 within the xy-plane in order to bring the focal point of objective 908 to the detection volume as determined by program 932.

The measurement beam which is received from base station 902 over optical fibre 966 is directed by optical elements 970 to objective 908. The portion of the measurement beam which passes through the objective opening of objective 908 travels along the optical axis of objective 908 and is focused within the detection volume.

This causes return radiation, which is collected by objective 908 and coupled into optical fibre 968 by means of optical elements 970. The return radiation, which is received by spectrometer 903 within base station 902 is analyzed in order to determine one or more properties of the blood flowing through the detection volume. This analysis is performed by program 962. The result of the analysis is displayed on display 960.

It is to be noted that for relative movement of the objective and the skin, in order to focus the laser beam within the volume of interest in the blood vessel, it is also possible to move the skin rather than the objective by means of a suitable mechanism.

In some cases a relative movement of the objective and the skin is not necessary at all. For example the measurement head may be placed on a body portion with relatively thick blood vessels which are relatively close to the skin surface such that repositioning is not required. Such a measurement may be conveniently performed inside the mouth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A method of determining a property of a substance, the method comprising the steps of:
   performing an optical detection step for determining a position of a volume of interest by means of an objective,
   moving the objective such that a focal point of the objective is positioned in the volume of interest,
   performing optical spectroscopic analysis to spectroscopically determine the property of the substance in the volume of interest by means of a measurement beam,
   wherein a coverage of the measurement beam is greater than the objective opening, and
   wherein the objective is moved relative to the measurement beam in a direction perpendicular to the measurement beam while the objective opening remains within the coverage of the measurement beam.

2. The method of claim 1, wherein the substance is a fluid flowing through a biological tubular structure, and further comprising the steps of:
   tracking a movement of the biological tubular structure by repetitively performing the optical detection step,
   moving the objective such that the focal point remains in the volume of interest.

3. The method of claim 1, wherein the optical detection step is performed by means of an imaging method.

4. The method of claim 1, wherein the spectroscopic analysis includes one of Raman spectroscopy, fluorescence spectroscopy, elastic scattering spectroscopy, infrared spectroscopy, or photo-acoustic spectroscopy is used for performing the optical spectroscopic step.

5. The method of claim 1, wherein the substance is blood and the volume of interest is located in a blood vessel.

6. A computer program product comprising program means for performing the steps of claim 1.

7. The computer program product of claim 6, the program means being adapted to control a second reflective optical element in order to direct the measurement beam from the second reflective optical element onto a first reflective optical element, such that the first reflective optical element directs the measurement beam to the objective opening, the measurement beam having a direction perpendicular to the optical axis of the objective when it impinges upon the first reflective optical element.

8. A spectroscopic system for determining a property of a substance comprising:
   an imaging system which monitors a position of a volume of interest,
   an objective having a focal point for performing an optical detection,
   a spectroscopic system including:
      a laser which provides a stationary, incident measurement laser beam that is larger than and encompasses the volume of interest and the objective, and
      a spectrometer which spectroscopically analyzes laser light returned from the volume of interest via the objective;
   an actuator which moves the objective and the focal point transversely relative to the stationary incident measurement laser beam;
   a controller responsive to the imaging system to control the actuator to move the objective such that the focal point is maintained positioned in the volume of interest.

9. The spectroscopic system of claim 8, wherein the actuator includes mechanical, electro mechanical and/or piezoelectric components.

10. The spectroscopic system of claim 8, further comprising a first reflective optical element to direct the stationary incident laser beam to and around the objective opening, the measurement beam having a direction perpendicular to the optical axis of the objective.

11. The spectroscopic system of claim 10, further comprising a second reflective optical element to direct the incident measurement laser beam to the first reflective optical element, the second reflective optical element being mounted rotatably.

12. A method of providing an in vivo analysis of blood comprising:
   using an imaging system to locate an objective relative to a blood vessel;
   moving the objective such that a focal point of the objective is aligned with the blood vessel;
   forming a feedback loop such that the position of the objective is compared to the position of the blood vessel after movement of the objective and the objective is moved again until the focal point aligns with the blood vessel;
   using a spectroscopic system to direct a laser light beam through the objective and onto the blood vessel; and
   using return light to perform a spectroscopic analysis of the blood in the blood vessel.

13. The method of claim 1, wherein the measurement beam remains stationary and the objective moves relative to the measurement beam such that when the volume of interest moves, the focal spot tracks the volume of interest.

14. A computer program product carrying a computer program for controlling a spectroscopic system to perform the method of claim 12.

15. An apparatus for providing in vivo analysis of blood, the apparatus comprising:
   an objective having a focal point;
   an imaging system that determines a current position of the objective relative to a target blood vessel;
   a feedback loop which compares the current position of the objective focal point relative to the target blood vessel and moves the objective until the focal point coincides with the target blood vessel;
   a laser that directs laser light through the objective to the focal point; and
   a spectrometer which analyzes light returned through the objective to determine one or more properties of blood in the target blood vessel.

16. The method of claim 12, wherein the laser light beam of the spectroscopic system is stationary and larger in cross section than the objective and the volume of interest and wherein moving the objective includes moving the objective relative to the stationary laser light beam.

17. The apparatus of claim 15, wherein the feed back loop moves the object transversely relative to the laser light beam.

18. The apparatus of claim 17, wherein the laser directs a stationary laser light beam that is larger than the objective through and around the objective.

* * * * *